United States Patent [19]

Ullman et al.

[11] 4,258,027

[45] Mar. 24, 1981

[54] MULTI-FRACTIONABLE TABLET STRUCTURE

[75] Inventors: Michael K. Ullman; Stephen T. David; Claude E. Gallian, all of Evansville, Ind.

[73] Assignee: Mead Johnson & Company, Evansville, Ind.

[21] Appl. No.: 121,615

[22] Filed: Feb. 14, 1980

Related U.S. Application Data

[63] Continuation-in-part of Ser. No. 24,139, Mar. 26, 1979, Pat. No. 4,215,104.

[51] Int. Cl.³ ............................................. A61K 9/44
[52] U.S. Cl. ........................................................... 424/15
[58] Field of Search ............................................ 424/15

[56] References Cited

U.S. PATENT DOCUMENTS

| | | | |
|---|---|---|---|
| D. 91,644 | 3/1934 | Blackstone | D16/3 |
| D. 201,497 | 6/1965 | Ninger | D16/3 |
| D. 202,467 | 10/1965 | Guilmot | D16/3 |
| D. 216,307 | 12/1969 | Ninger | D16/3 |
| D. 228,456 | 9/1973 | Ninger | D16/3 |
| D. 229,049 | 11/1973 | Roberts | D16/3 |
| 1,836,604 | 12/1931 | Meyer | 424/15 X |
| 2,052,376 | 8/1936 | Zellers | 424/15 X |
| 3,336,200 | 8/1967 | Kraus et al. | 424/15 X |
| 3,723,614 | 3/1973 | Langauer | 424/15 X |
| 3,883,647 | 5/1975 | Geller | 424/15 X |

FOREIGN PATENT DOCUMENTS

| | | | |
|---|---|---|---|
| 1200790 | 9/1965 | Fed. Rep. of Germany | 424/15 |
| 438385 | 5/1912 | France | |
| 352208 | 9/1937 | Italy | |
| 8869 | of 1889 | United Kingdom | |
| 808014 | 1/1959 | United Kingdom | 424/19 |
| 993291 | 5/1965 | United Kingdom | 424/15 |

*Primary Examiner*—Shep K. Rose
*Attorney, Agent, or Firm*—R. E. Carnahan; R. H. Uloth

[57] ABSTRACT

The invention disclosed provides a multi-fractionable tablet structure initially configured in a unitary dosage while having readily severable sub-dosage units as components thereof. Score markings are positioned variously about the tablet such as along the top and bottom surfaces thereof. Additionally, score markings may appear along opposite vertical side surfaces of the tablet. Special placement of the score markings readily permits alternatively an accurate equal bisectional or trisectional fracture of the tablet as may be desired for patient consumption.

17 Claims, 25 Drawing Figures

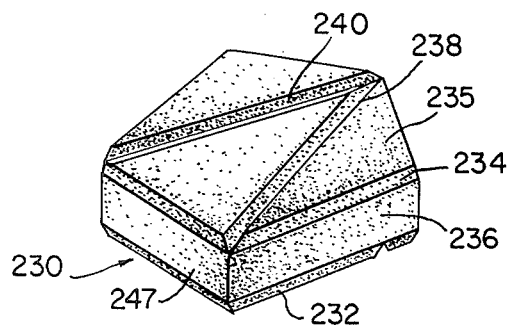
FIG. A.
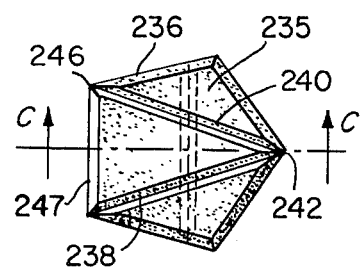
FIG. B.
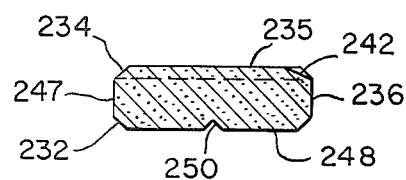
FIG. C.
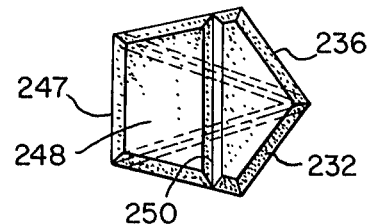
FIG. D.
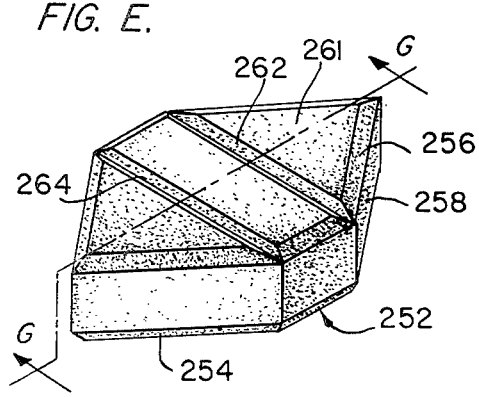
FIG. E.
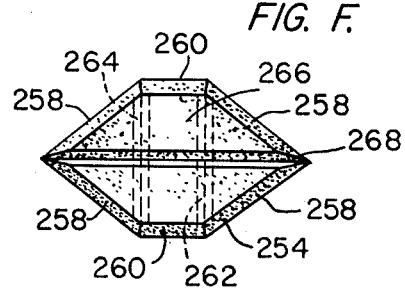
FIG. F.
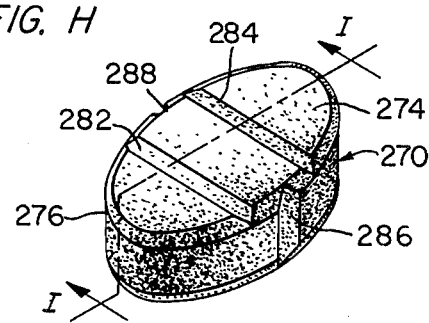
FIG. H.
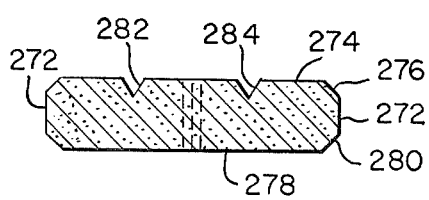
FIG. G.
FIG. I.
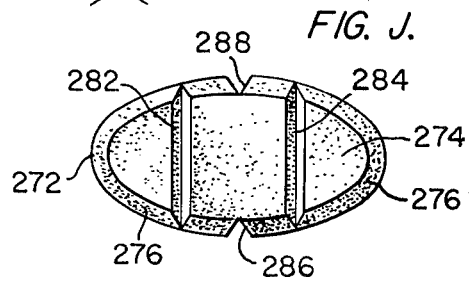
FIG. J.

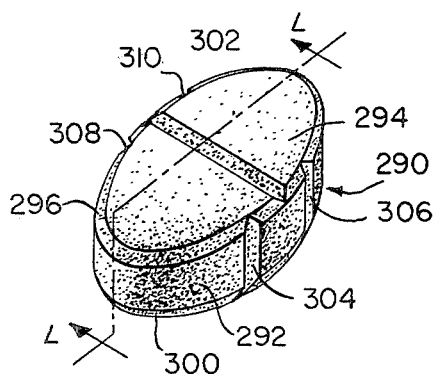
FIG. K.
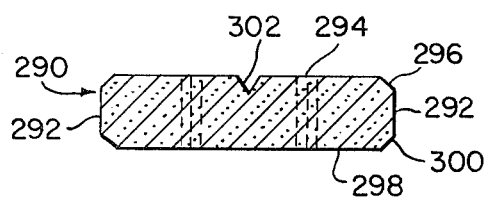
FIG. L.
FIG. M.
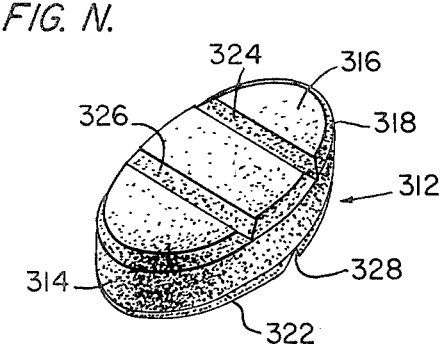
FIG. N.
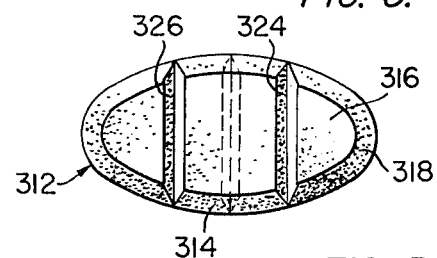
FIG. O.
FIG. P.
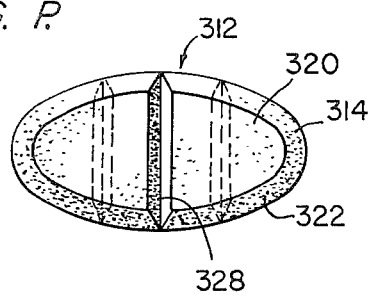
FIG. Q.
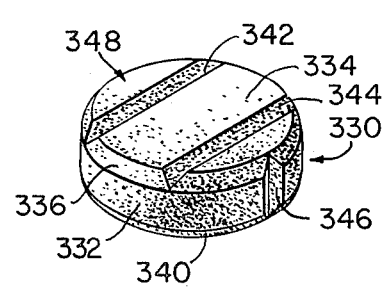
FIG. R.
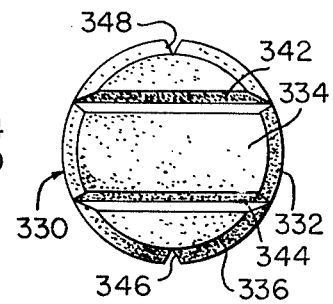
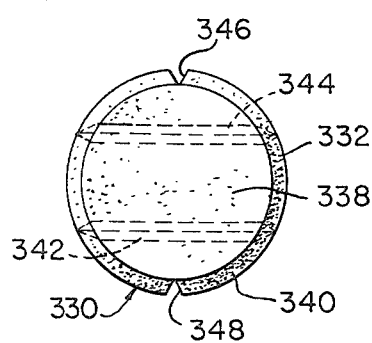
FIG. S.
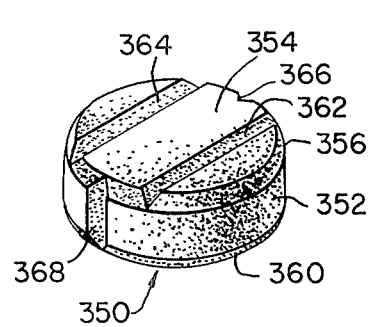
FIG. T.
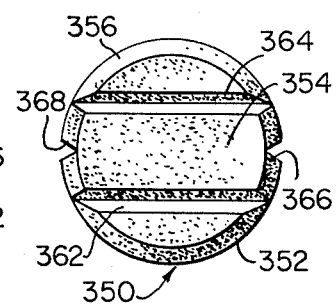
FIG. U.

FIG. V.
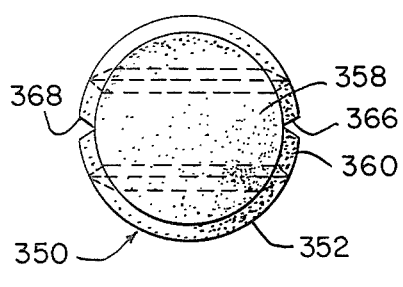
FIG. W.
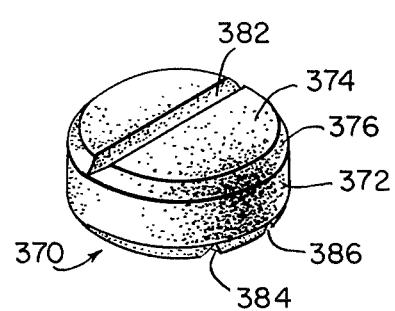
FIG. X.
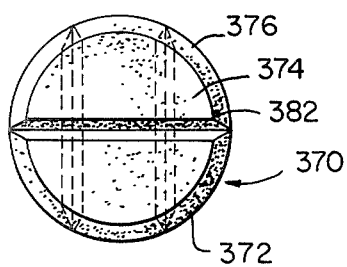
FIG. Y.
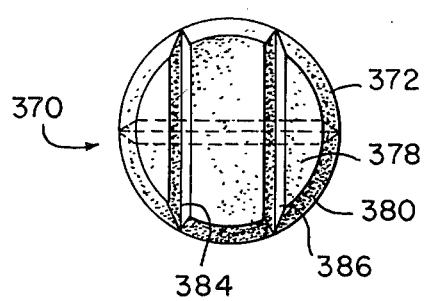

MULTI-FRACTIONABLE TABLET STRUCTURE

RELATIONSHIP TO PRIOR APPLICATION

This application for U.S. patent is a continuation-in-part of application Ser. No. 24,139, filed Mar. 26, 1979, now U.S. Pat. No. 4,215,104.

FIELD OF THE INVENTION

The present invention relates to a specially configurated multi-scored variously configurated tablet structure constituting a unitary dosage having readily severable sections which may be divided accurately and separated conveniently into multi-sectional sub-dosage units for patient consumption. The score markings are disposed specially such as along the top and bottom surfaces. Additionally, score markings may appear along opposite vertical side surfaces of the tablet.

BACKGROUND OF THE INVENTION

It is well known in the pharmaceutical art that tablets may be formed with a groove or score marking to facilitate breakage of the tablet into sub-dosage units. Typically, these tablets are configurated circularly with a transverse score marking disposed along the top surface of the tablet such that the tablet may be severed into half-sections. One example of such a tablet is that disclosed by Geller, in U.S. Pat. No. 3,883,647. Another example of a tablet having surface score lines and a circular configuration except severable into quarter-sections is the maltese-cross scored tablet disclosed by Languaer in U.S. Pat. No. 3,723,614.

Because of the inherent difficulties of breaking a grooved tablet into accurate predetermined parts, a variety of diverse attempts have been made in the prior art seeking tablet structures which are readily fractured into sub-dosage units by application of moderate manual pressure. One example of such an attempt is that disclosed by Kraus et al., in U.S. Pat. No. 3,336,200, where two half sections having a highly tapered top surface which join at a score line positioned along the diameter of the tablet. These diverse attempts to improve the convenience and accuracy of breaking a grooved tablet into predetermined parts have achieved limited success at best.

Inherently, the problem of breaking a grooved circular tablet resides in the hardness factor which results from tablet forming presses coupled with the small size configuration which does not allow for either ease of handling or breaking. A typical attempt to sever such circular tablet is by means of a sharp knife or related instrument which results more often than not, in facture of the tablet into undesired miniature pieces. In cases where the severing into two pieces is successful, the pressure which is required along the score marking frequently propels both sections from the initial location unless extreme care is used to contain the two pieces during the breaking operation.

In order to overcome the problem of breaking circular tablets because of the hardness factor and small size, prior art attempts have also been made to configurate oblong tablets having score lines disposed transversely along the top surface. One example of such a tablet is that disclosed by Zellers in U.S. Pat. No. 2,052,376. These oblong tablet configurations have also realized limited success in providing a solution to a readily, accurately severable unitary dosage tablet into sub-dosage units. Also, although tablets such as those disclosed by Zellers are oblong in appearance, the transverse cross-sectional configuration thereof is typically cylindrical. This configuration invites disadvantages associated with inclusion of sufficient amounts of active ingredients in a configuration which may be readily consumed without suffering patient discomfort.

One of the well recognized advantages of having a readily dividable tablet is that it permits the administration of a plurality of sub-dosage units thereby avoiding costs for specially preparing an individual tablet for each dosage unit.

It has now been found that by practice of the present invention, unitary dosage tablets may be prepared having specially disposed score markings which permit breakage of the unitary dosage tablet into multi-sectional sub-dosage units in a convenient, accurate manner. Thus, a number of the disadvantages inherent in prior art attempts to provide a solution to tablet breakage into accurate sub-dosage units which may be conveniently consumed by a patient have now been overcome by practice of the present invention.

SUMMARY OF THE INVENTION

The present invention generally stated provides a new, improved multi-scored tablet constituting a unitary dosage having readily severable sections which may be divided accurately and separated conveniently into multi-sectional sub-dosage units.

Generally, tablets of the present invention have score markings disposed selectively along top, bottom, and vertical wall surfaces of a unitary tablet body.

In one general embodiment, the present multi-fractionable tablet has a multi-angular configuration with specially disposed transverse score markings positioned along both the top, and bottom surfaces.

In another general embodiment, the present multi-fractionable tablet has an approximately circular or elliptical vertical wall configuration with two vertical score markings roughly equally positioned along opposite vertical side wall sections of the tablet with intermediately disposed score markings positioned along both the top and bottom surfaces thereof.

In yet another general embodiment, the present multi-fractionable table has an approximately circular or elliptical vertical wall configuration with two transverse score markings disposed along the top surface thereof and defining approximately equal trisectional dosage units in configuration with a longitudinal score marking disposed along the bottom surface of the tablet and defining approximately equal bisectional dosage units.

It is an object of the present invention to provide a multi-fractionable tablet structure prepared in a unitary dosage amount and having score markings disposed selectively such that the tablet may be conveniently fractured into multi-sectional dosage units as desired for patient consumption.

It is also an object of the present invention to provide a multi-fractionable unitary tablet body which may be readily prepared using conventional tablet forming presses, and yet provide a tablet having specially positioned score markings such that the unitary dosage tablet may be readily and conveniently fractured into at least either bisectional or tri-sectional dosage units as desired for patient consumption.

These and other objects and advantages of the present invention will become more readily apparent from the more detailed description of preferred embodiments taken in conjunction with the drawings wherein similar elements are identified by like numerals throughout the several views.

DESCRIPTION OF THE FIGURES

FIG. A is a perspective view of a multi-fractionable pharmaceutical tablet illustrating one embodiment of the present invention;

FIG. B is a top view of the pharmaceutical tablet of FIG. A;

FIG. C is a bottom view of the tablet of FIG. A;

FIG. D is a transverse cross-sectional view of the pharmaceutical tablet of FIG. B taken along sectional lines D—D, FIG. E is a perspective view of another embodiment multi-fractionable pharmaceutical tablet of the present invention;

FIG. F is a bottom view of the pharmaceutical tablet of FIG. E;

FIG. G is a longitudinal cross-sectional view of the pharmaceutical tablet of FIG. E taken along sectional lines G—G;

FIG. H is a perspective view of yet another embodiment multi-fractionable pharmaceutical tablet of the present invention;

FIG. I is a longitudinal cross-sectional view of the pharmaceutical tablet of FIG. H taken along sectional lines I—I;

FIG. J is a top view of the pharmaceutical tablet of FIG. H;

FIG. K is a perspective view of yet another embodiment multi-fractionable pharmaceutical tablet of the present invention;

FIG. L is a transverse cross-sectional view of the pharmaceutical table of FIG. K taken along sectional lines L—L;

FIG. M is a top view of the pharmaceutical tablet of FIG. K;

FIG. N is a perspective view of yet another embodiment multi-fractionable pharmaceutical tablet of the present invention;

FIG. O is a top view of the pharmaceutical tablet of FIG. N;

FIG. P is a bottom view of the pharmaceutical tablet of FIG. N;

FIG. Q is a perspective view of yet another embodiment multi-fractionable pharmaceutical tablet of the present invention;

FIG. R is a top view of the pharmaceutical tablet of FIG. Q;

FIG. S is a bottom view of the pharmaceutical tablet of FIG. Q;

FIG. T is a perspective view of yet another embodiment pharmaceutical tablet of the present invention;

FIG. U is a top view of the pharmaceutical tablet of FIG. T;

FIG. V is a bottom view of the pharmaceutical tablet of FIG. T;

FIG. W is a perspective view of yet another embodiment pharmaceutical tablet of the present invention;

FIG. X is a top view of the pharmaceutical tablet of FIG. W; and

FIG. Y is a bottom view of the pharmaceutical tablet of FIG. W.

DETAILED DESCRIPTION OF PREFERRED EMBODIMENTS

FIGS. A–D illustrate pharmaceutical table 230 having bevel edge 232 disposed about the bottom peripheral edge thereof with bevel edge 234 disposed about the peripheral edge of top surface 235. These bevel edges may vary as desired and typically range from about 25° to about 50° from the horizontal plane. The side walls of pharmaceutical tablet 230 define an approximate pentagon by wall surfaces 236. On the top surface 235 of tablet 230, there are disposed score 238 and score 240 which originate at one vertical wall edge 242 defining an apex and terminate at oppositely disposed vertical wall edges 244 and 246 respectively, defining base wall 247 of the pentagonal configuration.

Bottom surface 248 of pharmaceutical tablet 230 includes score line 250 which approximately parallels base wall 247.

For consumption purposes, pharmaceutical tablet 230 may be administered as a unitary dosage. In the event a partial dosage is desired, the tablet may be fractured conveniently along score markings 238, while an approximate one-third dosage may be administered by fracturing the tablet respectively along score markings 238 and 240. It will also be appreciated that an approximate one-half dosage may be administered by fracturing the tablet along score markings 250. In the event all of the score lines are used; namely, score lines 238, 240, and 250, it is then possible to provide as many as six multi-fracture dosages.

FIGS. E–G illustrate an embodiment pharmaceutical tablet 252 of the present invention having bevel edge 254, similar to that of tablet 230, disposed about the bottom peripheral edge, with bevel edge 256 correspondingly positioned about the top peripheral edge.

Pharmaceutical tablet 252 is illustrated with hexagonal vertical walls, wall members 258 being approximately equal in length and joined by shorter, parallel walls 260, so as to provide equal trisectional units when fractured along score lines 262 and 264. It will be apparent that parallel walls 260 may be of equivalent length or even longer than wall members 258 if desired. It is preferred to have two of the vertical wall members, such as walls 260, disposed in parallel when comprising the embodiment tablet of FIG. E–G. This feature expedites more effective fracture of this tablet along the top surface 261 by means of score lines 262 and 264 which join the apex where parallel walls 260 unite with wall members 258.

Disposed along the bottom surface 266 of pharmaceutical tablet 252 is score line 268 which joins the two apex sections formed where the respective pairs of wall members 258 unite.

When it is desired to fracture tablet 252 into multi-dosages, fracture may be effected along score lines 262 and 264 which results in up to three multi-dosage portions, or separately along score line 268 which results in two multi-dosage portions. Should one desire, fracture of tablet 252 may be effected along the top and bottom score lines in which case up to six multi-dosage portions result.

FIGS. H–J illustrate an elliptical embodiment pharmaceutical tablet 270 of the present invention having vertical walls 272, top surface 274 with bevel edges 276, and bottom surface 278 with bevel edges 280. The bevel edges are similar in configuration to those of pharmaceutical tablet 230 of FIGS. A–D.

On the top surface of pharmaceutical tablet 270 are two score lines 282 and 284, respectively with intermediately disposed vertical score lines 286 and 288. Score lines 286 and 288 are approximately oppositely positioned along vertical walls 272.

Fracture of the elliptical embodiment pharmaceutical tablet of FIGS. H–J may be effected along score lines 282 and 284 which provides three equal multi-dosage portions, or separately between score lines 286 and 288 which results in two equal multi-dosage portions.

FIGS. K–M illustrate another elliptical embodiment pharmaceutical tablet 290 of the present invention having vertical walls 292, top surface 294 with bevel edges 296, and bottom surface 298 with bevel edges 300. The bevel edges are similar in configuration to those of pharmaceutical tablet 230 of FIGS. A–D.

On the top surface of pharmaceutical tablet 290 is one intermediate score line 302, with two disposed vertical pairs of score lines 304 and 306, and 308 and 310, respectively. One pair of score lines 304 and 306 are approximately oppositely positioned along vertical walls 292 to the second pair of score lines 308 and 310.

Fracture of the elliptical embodiment pharmaceutical tablet of FIGS. K–M may be effected along the two sets of score lines 304 and 306, and 308 and 310 which provides three equivalent multi-dosage portions, or separately along score line 302 which results in two equivalent multi-dosage portions.

FIGS. N–P illustrate yet another elliptical embodiment pharmaceutical tablet 312 of the present invention having vertical walls 314, top surface 316 with bevel edges 318, and bottom surface 320 with bevel edges 322. Again, the bevel edges are similar in configuration to those of pharmaceutical tablet 230 of FIGS. A–D.

On the top surface 316 of pharmaceutical tablet 312 are two score lines 324 and 326, respectively, with intermediately disposed bottom score lines 328.

Fracture of the elliptical embodiment pharmaceutical tablet 312 of FIGS. N–P may be effected along score lines 324 and 326 which provides three equivalent multi-dosage portions, or separately along bottom score line 328 which results in two equivalent multi-dosage portions.

FIGS. Q–S illustrate a circular embodiment pharmaceutical tablet 330 of the present invention having vertical walls 332, top surface 334 with bevel edges 336, and bottom surface 338 with bevel edges 340. Again, the bevel edges are similar in configuration to those of pharmaceutical tablet 230 of FIGS. A–D.

On the top surface 334 of pharmaceutical tablet 330 are two score lines 342 and 344, respectively, with vertical wall score lines 346 and 348 positioned to effect a transverse breakage to that of score lines 342 and 344. Score lines 348 and 346 are approximately oppositely positioned along vertical wall surface 332.

Fracture of the circular embodiment pharmaceutical tablet 330 of FIGS. Q–S may be effected along score lines 342 and 344 which provides three equivalent multi-dosage portions, or separately along score lines 346 and 348 which results in two equivalent multi-dosage portions. Again, should one desire, fracture of tablet 330 may be effected along each of score lines 342–344 346–348 in which case up to six multi-dosage portions result.

FIGS. T–V illustrate another circular embodiment pharmaceutical tablet 350 of the present invention having vertical walls 352, top surface 354 with bevel edges 356, and bottom surface 358 with bevel edges 360. Again, the bevel edges are similar in configuration to those of pharmaceutical tablet 230 of FIGS. A–D.

On the top surface 354 of pharmaceutical tablet 350 are two score lines 362 and 364, respectiely, with vertical wall score lines 366 and 368 positioned to effect a parallel intermediate to that of score lines 362 and 364. Score lines 366 and 368 are approximately oppositely positioned along vertical wall surface 352.

Fracture of the circular embodiment pharmaceutical tablet 350 of FIGS. T–V may be effected along score lines 362 and 364 which provides three equivalent multi-dosage portions, or separately along score lines 366 and 368 which results in two equivalent multi-dosage portions.

FIGS. W–Y illustrate yet another circular embodiment pharmaceutical tablet 370 of the present invention having vertical walls 372, top surface 374 with bevel edges 376, and bottom surface 378 with bevel edges 380. Again, the bevel edges are similar in configuration to those of pharmaceutical tablet 230 of FIGS. A–D.

On the top surface 374 of pharmaceutical tablet 370 is one score line 382 with two bottom score lines 384 and 386 positioned to effect a transverse breakage to that of score line 382.

Fracture of the circular embodiment pharmaceutical tablet 370 of FIG. W–Y may be effected along score line 382 which provides two equivalent multi-dosage portions, or separately along score lines 184 and 186 which results in three equivalent multi-dosage portions. Again, should one desire, fracture of tablet 370 may be effected along side line 382 as well as along score lines 384 and 386 in which case up to six multi-dosage portions result.

The score markings may be at a V-groove angle of about 40° to 65°, and preferably about 45° to 60°, with each V-groove depth being about ⅛ to about ⅓ into the respective depth of the tablet.

The present multi-fractionable tablet structure includes specially positioned score markings for accurate multi-sectional fracture of the tablet.

Tablets of the present invention may be composed of a variety of ingredients such as one or more active pharmaceutical ingredients, fillers, lubricants, carriers, flavoring ingredients or the like as desired. These materials are well known to skilled tablet formulators.

Although it has not been specifically disclosed herein, it will be appreciated that the present multi-fractionable tablet structure may be specially marked with a corporate logo or otherwise colored as desired to reflect particular dosage units being consumed. Also, the present tablet may be coated with suitable materials well known in the tablet formation art.

Having described the present invention with particular reference to the disclosed embodiments, it will be obvious to those skilled in this art, that various changes and modifications may be made therein without departing from the spirit and scope of the invention which is disclosed and claimed herein.

What is claimed is:

1. A tablet structure which comprises a unitary body having oppositely disposed first and second substantially horizontal surfaces being joined respectively by substantially vertical walls; any one of said first horizontal surface, or said second horizontal surface, or said substantially vertical walls containing at least two transverse score markings and at least one other of said surfaces or walls containing a single transverse score marking whereby the unitary body may be fractured into at least equal bisectional or equal trisectional units for consumption.

2. The tablet structure of claim 1 wherein first and second surfaces include bevel edges, and wherein the score markings have an indentation depth to a line defining the bevel edge.

3. The tablet structure of claim 2 wherein the bevel edges range from about 25 degrees to about 50 degrees from the horizontal plane.

4. The tablet structure of claim 3 wherein the bevel edge angle is about 30 degrees to about 45 degrees.

5. The tablet structure of claim 1 wherein the score markings have a V-groove angle of about 40 degrees to about 50 degrees, with a V-groove depth being about ⅛ to about ⅓ the width of the tablet.

6. The tablet structure of claim 1 wherein the first and second surfaces define the top and bottom surfaces respectively.

7. The tablet structure of claim 1 wherein the substantially vertical walls define a pentagonal unitary body.

8. The tablet structure of claim 7 wherein said first substantially horizontal surface has two score lines disposed transversely from one apex defining joining vertical wall sections to opposite apexes defined by a common base vertical wall section to effect a trisectional fracture of the unitary body, and said second substantially horizontal surface has a single score to effect a transverse bisectional fracture of the unitary body.

9. The tablet structure of claim 1 wherein the substantially vertical walls define a hexagonal configuration.

10. The tablet structure of claim 9 wherein said first substantially horizontal surface has two parallel score lines disposed therein transversely from oppositely disposed apexes defined by common vertical wall structures, and a single score line disposed on said second substantially horizontal surface perpendicularly to said two parallel score lines.

11. The tablet structure of claim 1 wherein the substantially vertical walls define an elliptical configuration.

12. The tablet structure of claim 11 wherein said first substantially horizontal surface has one score line disposed thereon, and said vertical walls have two sets of oppositely positioned vertical score lines externally of said horizontal surface score line.

13. The tablet structure of claim 11 wherein said first substantially horizontal surface has two parallel score lines disposed thereon, and said second substantially horizontal surface has one score line intermediate said two parallel score lines.

14. The tablet structure of claim 1 wherein the substantially vertical walls define a circular configuration.

15. The tablet structure of claim 14 wherein said first substantially horizontal surface has two parallel score lines disposed thereon, and said vertical walls having two oppositely positioned vertical score lines disposed to effect a perpendicular fracture to said two parallel score lines.

16. The tablet structure of claim 14 wherein said first substantially horizontal surface has two parallel score lines disposed thereon, and said vertical walls have two oppositely positioned vertical score lines intermediate said two parallel score lines.

17. The tablet structure of claim 14 wherein said first substantially horizontal surface has one score line disposed thereon, and said second substantially horizontal surface has two parallel score lines disposed peripendicular to the score line on said first horizontal surface.

* * * * *

UNITED STATES PATENT AND TRADEMARK OFFICE
CERTIFICATE OF CORRECTION

PATENT NO. : 4,258,027
DATED : March 24, 1981
INVENTOR(S) : Michael K. Ullman, Stephen T. David, and Claude E. Gallian It is certified that error appears in the above—identified patent and that said Letters Patent is hereby corrected as shown below:

[*] Notice: The portion of the term of this patent subsequent to July 29, 1997, has been disclaimed.

Column 3, line 12, delete "C" and insert -- D --.

Column 3, line 13, delete "D" and insert -- C --.

Column 3, line 15, delete "D-D" and insert -- C-C --.

Column 7, line 3, after "wherein", insert -- said --.

Signed and Sealed this

Eighth Day of September 1981

[SEAL]

Attest:

GERALD J. MOSSINGHOFF

Attesting Officer     Commissioner of Patents and Trademarks